(12) United States Patent
Frezza

(10) Patent No.: US 8,118,788 B2
(45) Date of Patent: Feb. 21, 2012

(54) PRE-FILLED HYPODERMIC SYRINGE FITTED WITH A STOPPERING DEVICE

(75) Inventor: Pierre Frezza, Charly (FR)

(73) Assignee: Laboratoire Aguettant, Lyon (FR)

( * ) Notice: Subject to any disclaimer, the term of this patent is extended or adjusted under 35 U.S.C. 154(b) by 0 days.

(21) Appl. No.: 12/087,480

(22) PCT Filed: Jan. 19, 2007

(86) PCT No.: PCT/FR2007/000107
§ 371 (c)(1),
(2), (4) Date: Sep. 19, 2008

(87) PCT Pub. No.: WO2007/083034
PCT Pub. Date: Jul. 26, 2007

(65) Prior Publication Data
US 2009/0149817 A1    Jun. 11, 2009

(30) Foreign Application Priority Data
Jan. 19, 2006    (FR) ...................................... 06 00490

(51) Int. Cl.
*A61M 5/24* (2006.01)
(52) U.S. Cl. ............ 604/200; 604/82; 604/87; 604/111; 604/148; 604/199; 604/244; 604/905
(58) Field of Classification Search ............ 604/82, 604/87, 111, 148, 199, 200, 244, 905
See application file for complete search history.

(56) References Cited

U.S. PATENT DOCUMENTS

| 5,531,707 | A | * | 7/1996 | Kers et al. ..................... 604/200 |
| 6,068,614 | A | * | 5/2000 | Kimber et al. ................ 604/200 |
| 2004/0225258 | A1 | * | 11/2004 | Balestracci .................... 604/111 |
| 2005/0283116 | A1 | | 12/2005 | Eakins et al. | |

FOREIGN PATENT DOCUMENTS

| EP | 0 815 884 A1 | 1/1998 |
| EP | 1 166 742 A2 | 1/2002 |
| GB | 2 006 712 A | 5/1979 |
| NL | C 1021236 | 4/2004 |
| WO | WO 2005/123159 A2 | 12/2005 |

* cited by examiner

*Primary Examiner* — Bhisma Mehta
*Assistant Examiner* — Larry R Wilson
(74) *Attorney, Agent, or Firm* — Oliff & Berridge, PLC

(57) ABSTRACT

A pre-filled hypodermic syringe includes a tubular body having two open ends and containing a fluid to be administered to a patient; a plunger which, having at one of its ends a piston mounted to slide in the tubular body, passes through the opening of the first end of the tubular body; a tip for connection in the form of a cone of the Luer or Luer-Lock type, for example for connecting to a needle or to a drip, intended to pass the fluid that is to be administered and comprising a tubular part communicating with the opening of the second end; the tip comprising an obturator connected by a frangible region to the free end of its tubular part, the syringe being made of a synthetic material and obtained by molding, the obturator being molded as one piece with the tip and the tubular body.

11 Claims, 4 Drawing Sheets

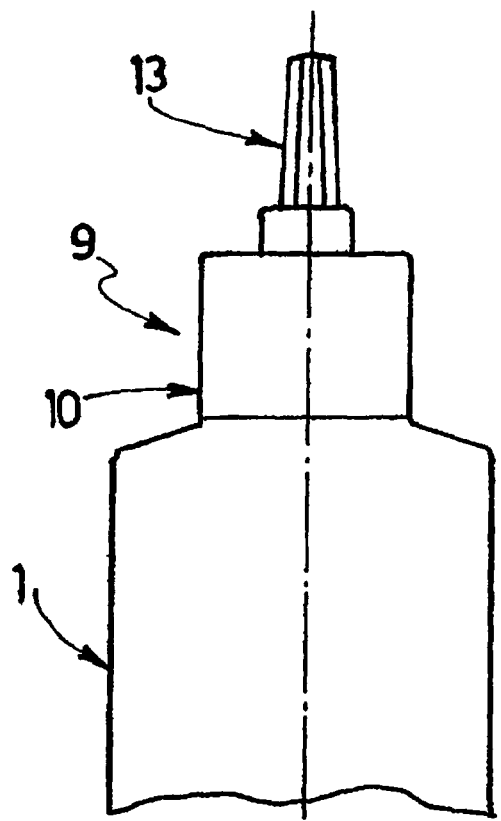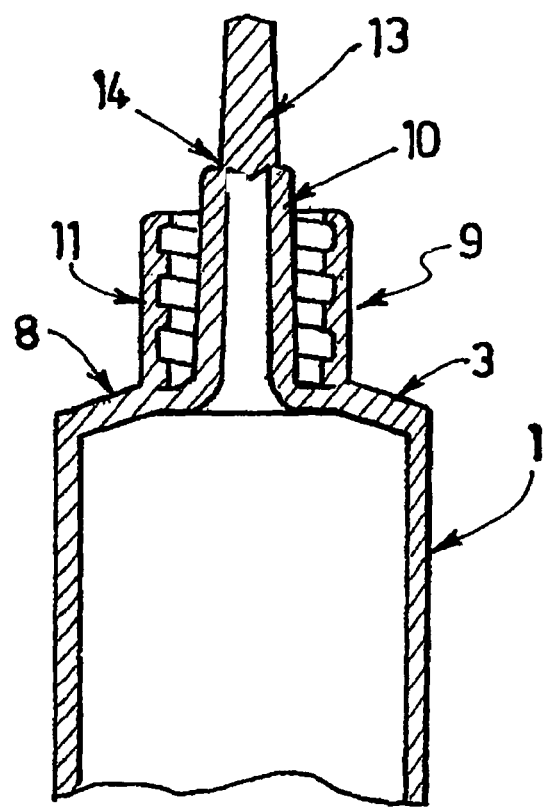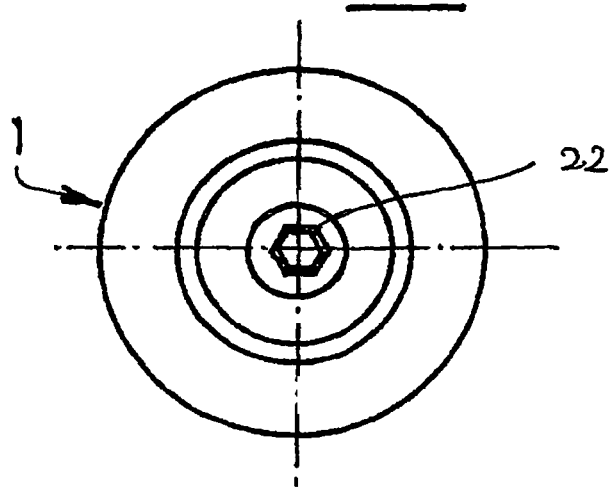

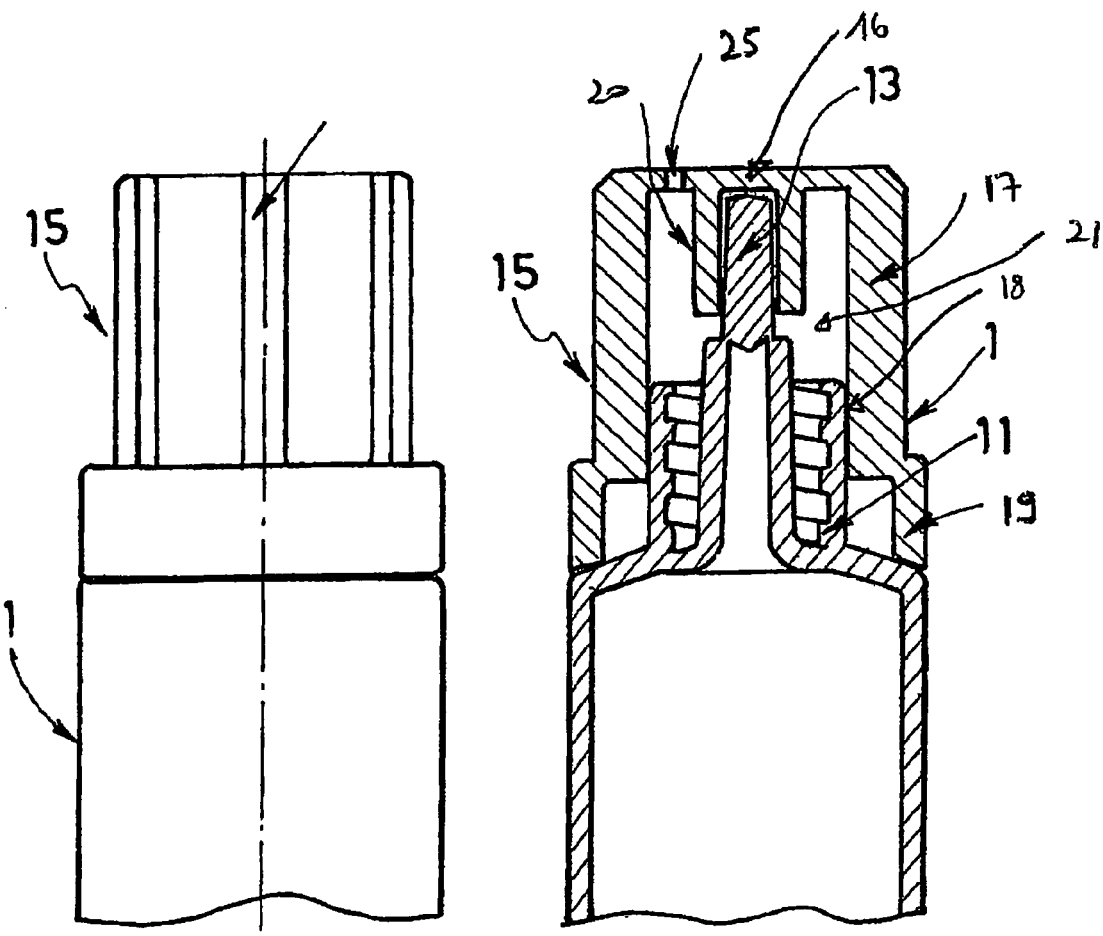
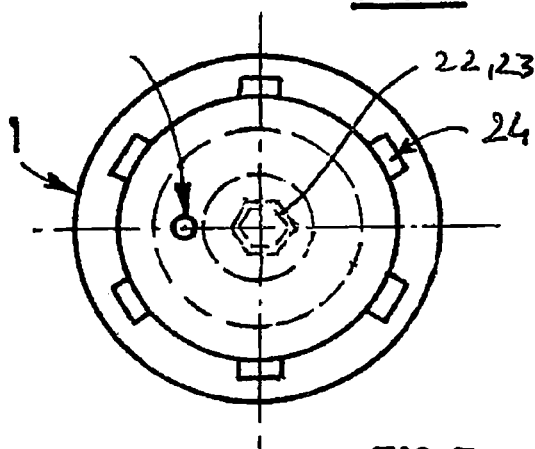
FIG.5  FIG.6
FIG.7

PRE-FILLED HYPODERMIC SYRINGE FITTED WITH A STOPPERING DEVICE

BACKGROUND OF THE INVENTION AND DESCRIPTION OF THE PRIOR ART

The invention relates to a pre-filled hypodermic syringe fitted with a stoppering device.

Pre-filled syringes are provided in the form of a standard syringe whose outlet end has a tip fitted with a removable stopper which is mounted sealingly thereon.

FIG. 1 shows such a pre-filled hypodermic syringe. The latter comprises a tubular body 1 with a generally cylindrical shape. This tubular body has a first open end 2.

A plunger 6 passes through the opening of the first end 2 of the tubular body 1. At its end mounted in the tubular body 1, the plunger 6 has a piston 4 which is able to slide inside the tubular body 1 in the longitudinal direction thereof. The plunger 6 thus allows the user to move the piston in translation.

The outer surface of the tubular body 1 has a flange 7 at the first end 2. The user's fingers are placed on the flange, and the piston 4 can be actuated by pressing on the end of the plunger 6 remote from the end connected to the piston 4.

The second end 3 of the tubular body has a wall 8 that is substantially transverse and open at its center.

The tubular body 1 additionally has a connection tip 9 of the Luer lock type arranged at its second end 3, on the outer face of the wall 8. As is known per se, the tip 9 is composed of a tubular part 10 and of a threaded part 11 forming a neck.

The tubular part 10 is of substantially conical shape, and the opening situated at the end of greater diameter of the tip is coincident with the opening of the wall 8.

The threaded part 11 of the tip is intended to allow a tip of complementary shape to be screwed on, allowing a needle or infusion line to be connected to the syringe. The threaded part 11 is arranged coaxially with respect to the tubular part 10 and outside of the latter.

A stopper 12 is screwed onto the tip 9, by means of the threaded part 11, thereby covering the opening of the tubular part 10 of the tip 9.

The tubular body 1, the piston 4, the wall 8, the tubular part 10 of the tip 9, and the stopper 12 thus delimit a leaktight space serving as a reservoir for a fluid that is to be administered to a patient.

The stopper 12 closing off the tubular part 10 of the tip 9 can be removed by unscrewing it. Once the needle or infusion line has been connected to the tip 9, the plunger 6 allows the operator to actuate the piston 4 and thus administer to the patient the fluid contained in the reservoir.

The advantage of a pre-filled syringe is that it avoids the user transferring a medicament from any given container into the syringe prior to use. These syringes generally have a gradation that permits the desired dosing.

The pre-filled syringe is packaged in a blister pack closed off by a cover made of peel-off paper. This paper has the particular feature of being permeable to water vapor but impermeable to microorganisms. The whole assembly is sterilized with wet heat, that is to say by the parts to be sterilized coming into contact with high-temperature vapor. This vapor originates from a chamber of an autoclave, passes through the peel-off cover and thus reaches the various parts of the syringe that are to be sterilized.

However, since the removable stopper is mounted in a leaktight manner on the tip, the zone situated between these two elements is not accessible to the vapor. The outer face of the tip cannot therefore be sterilized using the wet heat sterilization method.

The whole assembly therefore has to be sterilized with dry heat in such a way as to guarantee sterility between the stopper and the tip on which it is mounted.

This method requires a longer sterilization time than does sterilization with wet heat.

The longer sterilization time increases the cost of producing such a syringe. It also causes greater degradation of the plastic material of the body of the pre-filled syringe, thereby increasing the risk of products of degradation being released into the solution. In addition, the prolonged exposure to high temperatures causes unacceptable degradation of certain active principles.

A further problem arises from the syringe being closed by a stopper.

When a stopper made of plastic material, generally polypropylene, is used, it is normally screwed onto a tip of the Luer lock type.

Regardless of the tightening torque at the moment when the stopper is screwed onto the tip, a relaxation of the tightening is observed during sterilization. This relaxation is caused by softening of the polypropylene at high temperature, and this compromises the leaktightness between the stopper and the tip.

In the case where a stopper made of elastomer is mounted by elastic clamping on the tip, the stopper is not affected by the rise in temperature. However, the sterilization creates an adherence of the stopper to the tip, making it difficult for the user to remove the stopper.

Document US 2005/0283116 describes a pre-filled hypodermic syringe comprising:
- a tubular body having two open ends and containing a fluid to be administered to a patient,
- a plunger which, at one of its ends, has a piston mounted slidably in the tubular body and which passes through the opening of the first end of the tubular body,
- a connection tip in the form of a cone of the Luer or Luer-lock type, for example for connection to a needle or infusion line, which connection tip is intended for passage of the fluid to be administered and comprises a tubular part communicating with the opening of the second end,
- the tip comprising an obturator connected by a frangible zone to the free end of its tubular part,
- the syringe being made of synthetic material and produced by molding, the obturator being molded in one piece with the tip and the tubular body, the syringe comprising a cap mounted on the tip.

The syringe is produced by molding, the outer forms of the syringe being delimited in a conventional manner by the walls of a mold, a core delimiting the inner volume of the tubular body and of the tubular part of the tip. In order to compensate for the dimension tolerances and for the deviations in the positioning of the core in the mold, the frangible zone formed at the end of the tubular part of the tip must necessarily have a sufficient thickness to ensure continuity of the material, even in the event of a fault in the positioning of the core.

The obturator is withdrawn by tilting it sideways with the aid of a cap provided with a slit.

In this case, the frangible zone connecting the obturator to the tip is subjected to heterogeneous stresses, namely tensile stresses on the one hand and compression stresses on the other. The poor distribution of the stresses in the frangible zone makes it uncertain that the frangible zone will be broken completely by a single tilting movement, which generally forces the user to perform an alternative movement. The presence of a thickness of material at the level of the frangible zone makes it all the more difficult to cleanly separate the obturator and the tip.

If a clean break is not obtained, particles may be produced when the tip is torn off, such that the solution contained in the syringe is contaminated.

The present invention therefore seeks to overcome these disadvantages by making available a syringe which can be sterilized easily and without extra expense and whose content is not affected by the sterilization, and which provides complete leaktightness while at the same time allowing the obturator and the tip to be separated efficiently.

SUMMARY OF THE INVENTION

To this end, the invention relates to a pre-filled hypodermic syringe of the aforementioned type, characterized in that the cap has a zone of fixation or coupling to the obturator such that the rotation of the cap about its longitudinal axis moves the obturator in rotation, in such a way as to cause the frangible zone to rupture.

The torque exerted on the obturator during rotation thereof about the longitudinal axis results in a homogeneous distribution of the stresses in the frangible zone.

The severing is thus obtained with limited effort and cleanly, that is to say without production of parasite particles or formation of irregularities in the frangible zone.

In addition, with this type of syringe it is easy to overcome the deviations in terms of dimensions and tolerances generated during manufacture. This is because an asymmetry of the frangible zone has little effect on the severing thereof, on account of the good distribution of the stresses.

Advantageously, the connection between the tubular part of the tip and the obturator is formed by an annular thinning of the material along the line of connection between the free end of the tubular part of the tip and the obturator.

According to a first embodiment, the cap has an end wall from which there protrudes a hollow stub which, when engaged on the obturator, cooperates with the latter through matching shape in such a way as to form a rotation coupling.

Preferably, the obturator and the hollow stub have matching polygonal shapes, for example hexagonal shapes.

Advantageously, the obturator and/or the hollow stub have a conical shape.

This feature allows the obturator to be engaged with a force fit in the hollow stub in such a way that, after rupture of the frangible zone, the obturator is maintained in the hollow stub and cannot fall off.

According to a second embodiment, the cap is fixed on the obturator by welding or adhesive bonding.

The two abovementioned embodiments allow the obturator and the tip to be separated by way of a protective cap. For this reason, the obturator can be removed by the user without risk of contact with the tubular element of the tip, thereby avoiding any bacterial contamination of the fluid passing to the needle or infusion line via the tubular element of the tip.

According to one feature of the invention, the cap has ergonomic means of rotation, facilitating the rotation of the cap and, consequently, the opening of the syringe by removal of the obturator.

Preferably, the cap comprises at least one orifice for passage of a sterilization fluid.

This orifice allows the vapor to easily access the parts that are to be sterilized and that are partially or completely covered by the cap. It is in this way that, during sterilization with wet heat, the vapor originating from the autoclave passes through the orifice of the cap and is directed in particular toward the outer surfaces of the tip.

Advantageously, the cap comprises a skirt extending as far as the body of the syringe, the part of the skirt situated toward the body of the syringe having, over at least part of its length, substantially the same cross section as the body of the syringe, the latter comprising a tamper-proof ring extending partly on the body of the syringe and partly on the skirt of the cap.

By means of this tamper-proof ring, the user is guaranteed the sterility of the parts of the syringe that are protected by the cap.

The invention will be clearly understood anyway from the following description in which reference is made to the attached schematic drawing showing, as non-limiting examples, several embodiments of this syringe.

BRIEF DESCRIPTION OF THE DRAWINGS

FIGS. 2, 3 and 4 are enlarged views of the end area comprising the tip of a syringe according to the invention not fitted with the cap, seen in a side view, in longitudinal section and in an end view, respectively;

FIGS. 5, 6 and 7 are views, corresponding respectively to FIGS. 2, 3 and 4, of the syringe fitted with the cap;

DESCRIPTION OF THE PREFERRED EMBODIMENT

Figure 1:
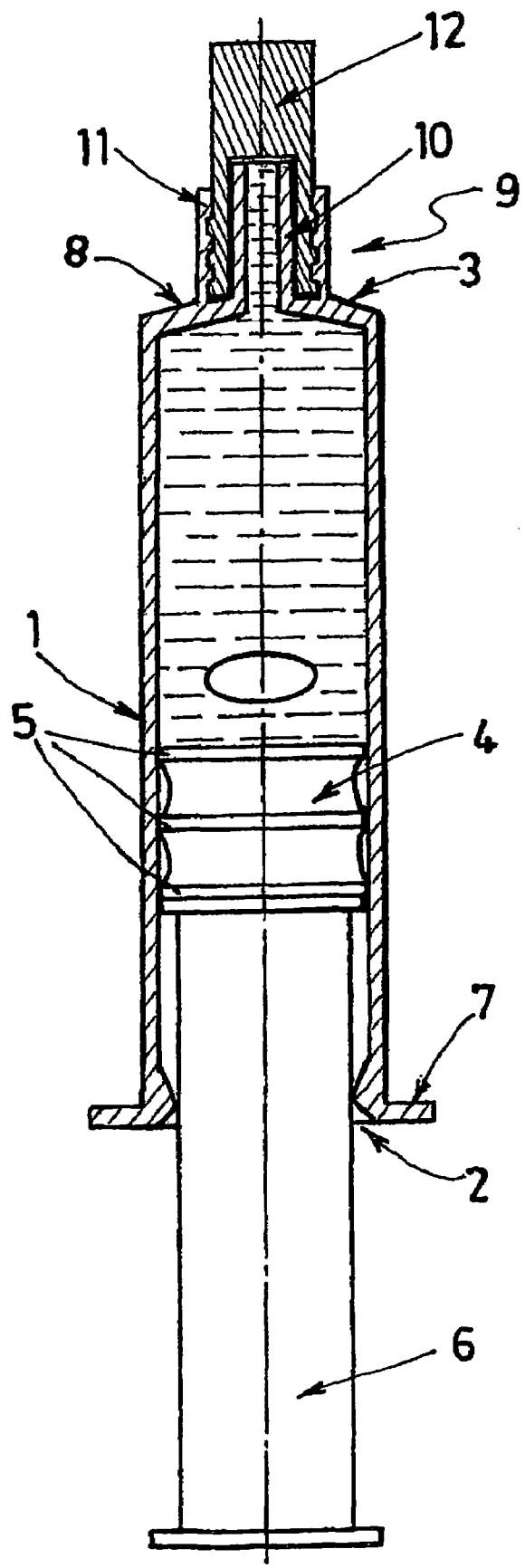
FIG. 1 is a longitudinal sectional view of a syringe of the prior art.

A hypodermic syringe according to the invention is shown in FIGS. 2 to 9, in which the same elements are designated by the same reference numbers as in FIG. 1.

FIGS. 2 and 3 show a hypodermic syringe which, as is known per se and as has been described previously, comprises a tubular body 1 with an open end 3 at which a tip 9 of the Luer lock type 9 is arranged.

The tip 9 comprises a tubular part 10 communicating with the opening of the wall 8, and an obturator 13 connected via a frangible zone to the free end of the tubular part 10.

The tubular body, the tip and the obturator are made of synthetic material and are produced in one piece by molding.

The frangible zone 14 between the tubular part 10 and the obturator 13 is formed by an annular thinning of the material along the line of connection between the free end of the tubular part 10 and the obturator 13. This makes it possible to separate these two parts, since the thinned area has a low resistance to tearing or rupturing under the effect of twisting.

As is shown in FIGS. 5 to 9, a cap 15 is fitted on the tip in order to make it easier to withdraw the obturator 13 while at the same time maintaining sterility.

The cap 15 has a generally cylindrical shape. It comprises an end wall 16 from which there protrudes a skirt 17 intended to engage on the outer wall 18 of the neck formed by the threaded part 11. The internal diameter of the skirt 17 is adapted in such a way as to permit a light clamping of the skirt 17 on the neck 11.

The skirt 17 extends as far as the body 1 of the syringe, and the free end 19 of the skirt 17, situated toward the body 1 of the syringe, has substantially the same external diameter as the body 1. This ensures a continuity of surface at the join between the tubular body 1 of the syringe and the skirt 17 of the cap 15.

The cap 15 additionally comprises a cylindrical hollow stub 20 protruding from the end wall 16 of the cap 15, in the internal volume 21 of the cap 15 delimited by the skirt 17.

The hollow stub 20 is centered on the longitudinal axis of the cap and engaged on the obturator 13.

As is shown in FIGS. 4 and 7, the obturator 13 and the hollow stub 20 have matching polygonal shapes 22, 23, for example hexagonal shapes. In addition, these two parts 13, 20 have slightly conical shapes to ensure a force-fit engagement of the obturator 13 in the hollow stub 20.

According to another variant of the invention, not shown here, the hollow stub 20 is fixed on the obturator 13 by adhesive bonding or welding.

The cap 15 also has flutings 24 that are arranged on the outer side thereof and that form ergonomic means for turning it.

The rotation of the cap 15 about its longitudinal axis moves the obturator 13 in rotation, and this causes the frangible zone 14 to rupture.

The cap 15 is then removed with the obturator 13, the latter being retained in the hollow shaft on account of the force-fit engagement, in such a way as to free the tubular part 10 of the tip 9 for connection of the needle or the infusion line leading to the patient.

The cap additionally comprises an orifice 25 intended for the passage of the sterilization fluid. During sterilization with wet heat, the vapor can thus pass from outside the cap 15 to the areas of the tip 9 that are to be sterilized.

Figures 8, 9:
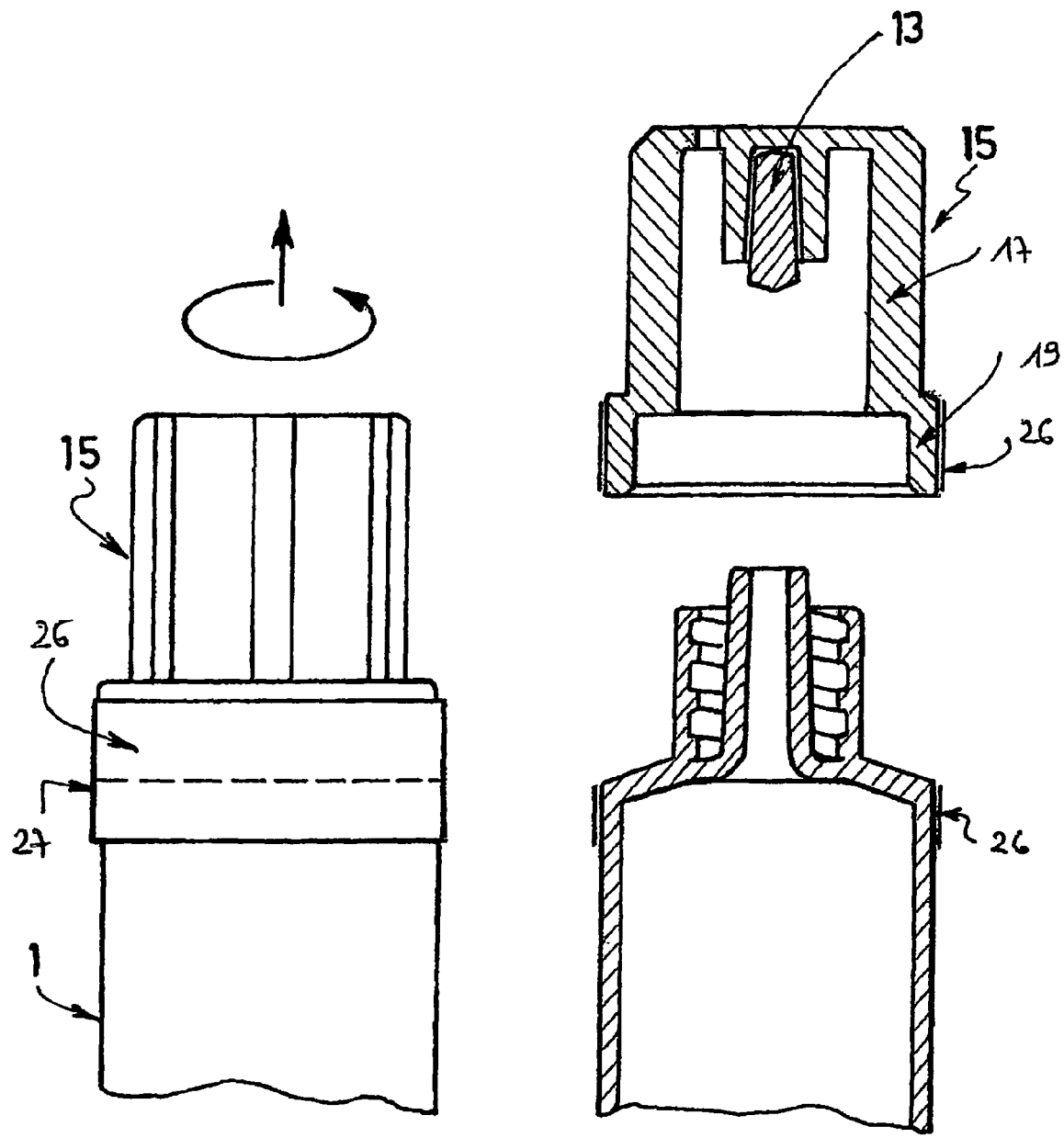
FIG. 8 is a view corresponding to FIG. 5, the syringe comprising a tamper-proof ring.
FIG. 9 is a view corresponding to FIG. 6, the obturator having been withdrawn from the tip by severing or tearing.

As has been shown in FIGS. 8 and 9, a tamper-proof ring 26 is mounted on the periphery of the tubular body 1 and of the skirt 17 of the cap 15 and extends partly on the tubular body 1 and partly on the skirt 17 in the area of its free end 19. The tamper-proof ring comprises a peripheral break area 27 situated along the line of connection between the cap 15 and the tubular body 1.

The rotation of the cap 15 makes it possible at one and the same time to sever the tamper-proof ring 26 and the connection area 14 between the obturator 13 and the tubular part 10 of the tip 9.

It will be appreciated that the invention is not limited only to the embodiments of this system that have been described above by way of example, and that instead it covers all variants thereof. Thus, the hollow stub and the obturator could have other kinds of shapes that permit coupling of these parts in rotation, such as flutings and matching grooves.

The invention claimed is:

1. A pre-filled hypodermic syringe molded of synthetic material comprising:
    a tubular body having an open first end and an open second end and containing a fluid to be administered to a patient,
    a plunger which, at one of its ends, has a piston mounted slidably in the tubular body and which passes through the opening of the first end of the tubular body,
    a connection tip in the form of a cone of a Luer-lock type, the connection tip is configured for the passage of the fluid that is to be administered and comprises a tubular part communicating with the opening of the second end, and a threaded part forming a neck and surrounding the tubular part, wherein
    the tip comprises an obturator connected by a frangible zone to the free end of the tubular part,
    the obturator is molded in one piece with the tip and the tubular body,
    the syringe comprises a cylindrical cap mounted on the tip, the cap has a zone of fixation or coupling to the obturator, such that rotation of the cap about its longitudinal axis moves the obturator in rotation in such a way as to cause the frangible zone to break, the zone of fixation or coupling is configured to form a hollow stub, the hollow stub is secured to the obturator, the obturator is non-rotatable relative to the hollow stub, and
    the syringe comprises a tamper-proof ring extending partly on the body of the syringe and partly on a skirt of the cap.

2. The hypodermic syringe as claimed in claim 1, wherein the join between the tubular part of the tip and the obturator is formed by an annular thinning of the material along the line of connection between the obturator and the free end of the tubular part of the tip.

3. The hypodermic syringe as claimed in claim 1, wherein the hollow stub cooperates with the obturator through having a matching shape, in such a way as to form a rotation coupling.

4. The hypodermic syringe as claimed in claim 3, wherein the obturator and the hollow stub have matching polygonal shapes.

5. The hypodermic syringe as claimed in claim 3, wherein the obturator and/or the hollow stub have a conical shape.

6. The hypodermic syringe as claimed in claim 1, wherein the cap is secured on the obturator by welding or adhesive bonding.

7. The hypodermic syringe as claimed in claim 1, wherein the cap has ergonomic means for rotating it.

8. The hypodermic syringe as claimed in claim 1, wherein the skirt of the cap is engaged on an outer wall of the threaded part forming the neck, the skirt extending toward the body of the syringe and covering substantially the entirety of the threaded part, the skirt comprising a part, situated toward the body of the syringe, having substantially the same cross section as the body of the syringe.

9. The hypodermic syringe as claimed in claim 1, wherein the tamper-proof ring and frangible zone are configured to break simultaneously.

10. The hypodermic syringe as claimed in claim 1, wherein the connection tip is connected to a needle or to an infusion line.

11. A pre-filled hypodermic syringe molded of synthetic material comprising:
    a tubular body having an open first end and an open second end and containing a fluid to be administered to a patient,
    a plunger which, at one of its ends, has a piston mounted slidably in the tubular body and which passes through the opening of the first end of the tubular body, and
    a connection tip in the form of a cone of a Luer-lock type, the connection tip is configured for the passage of the fluid that is to be administered and comprises a tubular part communicating with the opening of the second end, and a threaded part forming a neck and surrounding the tubular part, wherein
    the tip comprises an obturator connected by a frangible zone to a free end of the tubular part,
    the obturator is molded in one piece with the tip and the tubular body,
    the syringe comprises a cylindrical cap mounted on the tip, the cap has a zone of fixation or coupling to the obturator, such that the rotation of the cap about its longitudinal axis moves the obturator in rotation in such a way as to cause the frangible zone to break, the zone of fixation or coupling is configured to form a hollow stub, the hollow stub is secured to the obturator, the obturator is non-rotatable relative to the hollow stub,
the syringe comprises a tamper-proof ring extending partly on the body of the syringe and partly on a skirt of the cap, and
the cap has at least one orifice opening into an internal volume of the cap delimited by the skirt and the connection tip for passage of a sterilization fluid.

* * * * *